United States Patent [19]

Näslund

[11] Patent Number: 4,600,040

[45] Date of Patent: Jul. 15, 1986

[54] ARRANGEMENT IN APPARATUS FOR PREPARING SOLUTIONS FROM HARMFUL SUBSTANCES

[76] Inventor: Jan I. Näslund, Vassvägen 21, S-141 39 Huddinge, Sweden

[21] Appl. No.: 586,547

[22] Filed: Mar. 5, 1984

[30] Foreign Application Priority Data

Mar. 21, 1983 [SE] Sweden ................................ 8301517
Oct. 25, 1983 [SE] Sweden ................................ 8305867

[51] Int. Cl.⁴ ................................................ A61M 5/00

[52] U.S. Cl. ...................................... 141/18; 141/329; 604/411; 604/415

[58] Field of Search ....................... 141/5, 27, 52, 329, 141/18; 604/408, 411, 414, 415, 416

[56] References Cited

U.S. PATENT DOCUMENTS

| | | | |
|---|---|---|---|
| 921,130 | 5/1909 | Lockwood | 141/329 X |
| 2,689,562 | 9/1954 | Adams et al. | 604/415 X |
| 3,416,528 | 12/1968 | Kahn | 141/329 X |
| 3,661,189 | 5/1972 | Bowser et al. | 141/329 X |
| 3,882,909 | 5/1975 | Ogle | 141/329 X |
| 4,381,776 | 5/1983 | Latham, Jr. | 604/411 X |
| 4,509,861 | 4/1985 | Sjönell | 141/27 X |

*Primary Examiner*—Stephen Marcus
*Assistant Examiner*—Mark Thronson
*Attorney, Agent, or Firm*—Andrus, Sceales, Starke & Sawall

[57] ABSTRACT

An arrangement in apparatus for preparing solutions from dry harmful materials, such as cytostaticum, radioactive, toxic and allergy-producing substances, includes a glass ampoule (1) for accommodating the dry substance. The ampoule communicates with a device (4) for enlarging the internal volume of the ampoule, so as to equalize the pressure generated therein when preparing the solution.

Solvent is introduced into the ampoule (1) and solution removed therefrom through a cannula (8) which is constantly sheathed against contamination by means of an elastic sheath (10). The sheath is provided with self-sealing means (11) arranged to sealingly abut the ampoule (1) when withdrawing solution therefrom, in a manner to tightly seal the ampoule against the surroundings.

5 Claims, 4 Drawing Figures

ARRANGEMENT IN APPARATUS FOR PREPARING SOLUTIONS FROM HARMFUL SUBSTANCES

The present invention relates to an arrangement in apparatus for preparing solutions from harmful materials, such as cytostaticum, and radioactive, toxic, or allergy-producing substances, and particularly for the preparation of solutions from cytostaticum in dry-substance form.

Cytostaticum used for treating tumorous illnesses is stored dry in glass ampoules, and is mixed with a solvent immediately prior to use, so as to provide a cytostaticum solution. When the solvent is injected into the ampoule, which is inherently rigid, the air in the ampoule is compressed and the pressure in the ampoule will rise above the ambient pressure by from 1 to 2 atmospheres. Consequently, there is a grave risk that the cytostaticum (cellpoison) will spurt into the face of the person preparing the solution. Consequently, as a guard against personal injury, the solution is normally prepared under the cover of a screen in a basket funnel or a closed hood, and a closed system of interconnected tubes is arranged between the ampoules. The actual problem concerned, i.e. the problem of the overpressure prevailing in the ampoule, has not hitherto been solved.

In Swedish Published Specification No. 341 982 there is described an arrangement in ampoules for containing injection solutions, by means of which the creation of a partial vacuum in the ampoule as the solution is drawn into a syringe can be avoided. This known arrangement comprises a cannula and a capsule provided with an air filter made of fibre-glass paper, the cannula being inserted down through the capsule of the ampoule when filling the syringe. Thus, this known arrangement is intended for solving problems relating to pressures below ambient pressure.

Consequently, in accordance with a first aspect of the present invention, a primary object is to provide an arrangement in which the problem created by the air overpressure in the ampoule is eliminated.

When treating patients with cytostaticum solutions, or indeed with many other solutions, it is often necessary to fill a plurality of ampoules, in order to have the prescribed amount of solution available. This prescribed amount of solution is then drawn into a syringe, the volumetric capacity of which is sufficient to accommodate the solution. When withdrawing the cannula and trocar from respective ampoules, however, there is a grave risk that some of the solution will escape. There is also a grave risk that during their passage into and out of the respective ampoules, the cannula and trocar will become contaminated, by contact with contaminated surfaces. Consequently, in accordance with a second aspect of the invention, it is a further object to provide a complete arrangement of apparatus in which the harmful substance, e.g. a cytostaticum solution, can be handled safely and the aforementioned risks are eliminated.

The objects according to the aforesaid aspects of the invention are realized by means of an arrangement of apparatus according to the invention, which comprises a glass ampoule, or some other suitable rigid container, which is intended to accommodate said harmful substance; hermetically sealed means arranged for movement into and out of said ampoule, to introduce a solvent thereinto and withdraw solution therefrom; and hermetically sealed means communicating with said ampoules to enlargen the volume thereof, so as to equalize the pressure generated therein when preparing said solution.

The volume-enlarging means may conveniently comprise an expandable container located externally of the ampoule and arranged to communicate therewith through a suitable hose arrangement, in a hermetically sealed manner. This container may have the form of a bag made from a flexible material, and the hose means may comprise a further cannula.

According to one embodiment of the invention, the hermetically sealed means arranged for passage into and out of the ampoule comprises a cannula which is sheathed in a casing of elastic material, such as constantly to protect the cannula from contact with surrounding surfaces when moved into and out of the ampoule. This sheathing may be provided with a self-sealing thickened portion arranged to sealingly abut the capsule of the ampoule when introducing the cannula thereinto.

So that the invention will be more readily understood and further advantages afforded thereby made apparent, an embodiment of the invention will now be described with reference to the accompanying drawings, in which FIG. 1 is a schematic illustration of a glass ampoule containing dry cytostaticum, and of a cannula enclosed in an elastic sheath;

Figure 1:
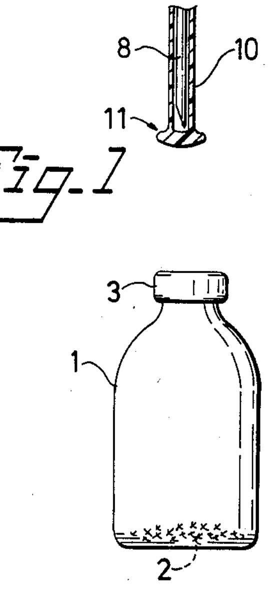
Figure 2:
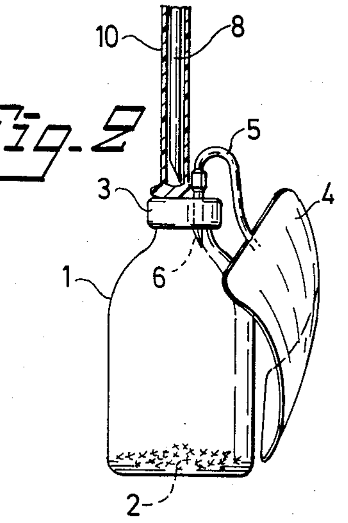
FIG. 2 is a schematic illustration of the ampoule in FIG. 1 provided with a volume-enlarging means in accordance with the invention.

The arrangement of apparatus illustrated in FIG. 1 includes an ampoule 1, which contains dry cytostaticum 2, and which is hermetically sealed by a capsule 3. As will be seen from FIG. 2, arranged externally of the ampoule 1 is a volume-enlarging means 4, which communicates with the ampoule 2 through a hose 5 and a cannula 6. The means 4 preferably has the form of an expandable container, such as a flexible bag made of some suitable material, such as plastics foil. In this way, the overpressure generated when injecting solvent into the ampoule will be equalized when air passes into the volume-enlarging means, which will inflate.

Figure 3:
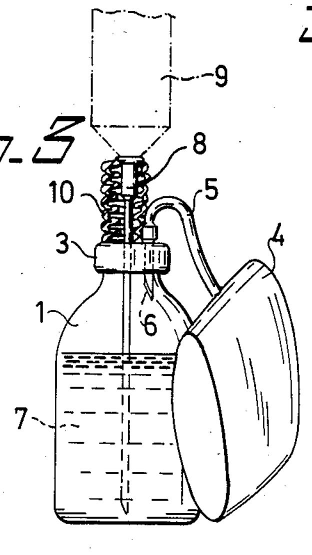
FIG. 3 is a view similar to FIG. 2, illustrating how a solvent is introduced into the ampoule with the aid of a cannula

As illustrated in FIG. 3, the solvent is introduced into the ampoule 1, to form a cytostaticum solution 7, through a further cannula 8 which is passed through the capsule 3 and into the ampoule. The solution is withdrawn from the ampoule by means of a syringe 9 connected to the cannula 8. When the solution is withdrawn from the ampoule 1 with the aid of the syringe 9, the gas located in the expandable container 4 will pass back to the ampoule 1, and the container will return to its original shape.

As will be understood, unless effective measures are taken, the cannula 8 when passing into and out of the ampoule 1 is likely to come into contact with contaminating surfaces. Such contamination of the cannula would require it to be sterilized. Consequently, in accordance with the aforesaid second aspect of the invention, the cannula 8, together with its trocar, is located in a sheath 10 which is made of an elastic, deformable material. The end of the sheath adjacent the trocar of the cannula 8 is provided with a self-sealing thickened portion 11, which is arranged to be brought into tight and sealing abutment with the outer surface of the capsule 3 prior to introducing the cannula 8 into the ampoule 1. As the cannula is pushed into the ampoule 1, the thickened portion will spread against its inherent springiness, such as to form an effective seal between the cannula-sheath-arrangement and the capsule 3.

Figure 4:
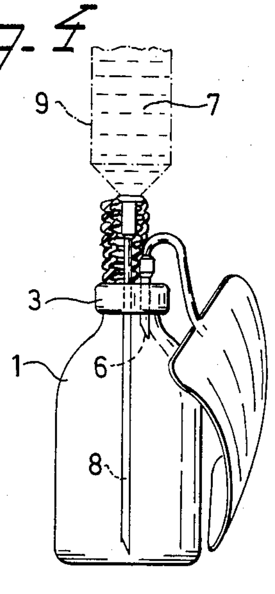
FIG. 4 is a view similar to FIG. 3, showing how cytostaticum solution is drawn into a syringe connected to the cannula.

As beforementioned, the sheath is made of an elastically, deformable material, and as the cannula 8 is pushed into the ampoule 1, the sheath will fold in a concertina fashion, as illustrated in FIGS. 3 and 4, to constantly protect the cannula against contact with contaminated surfaces. When the cannula is withdrawn, subsequent to preparing the solution, the sheath 10 will follow the movement of the cannula and return to its original shape, without exposing the cannula to the surroundings. When the cannula 8 has been totally withdrawn into its sheath 10, the cannula remains effectively protected against contamination and the solution contained in the cannula and the syringe 9 is hermetically sealed-off within the confines of the sheath 10. It will be understood that the fine aperture made by the trocar in the thickened portion 11 as the cannula is moved into the ampoule 1 will automatically close when the cannula is fully withdrawn into the sheath, as a result of the elasticity of the material from which the sheath is made.

Consequently, the aforedescribed sheath arrangement prevents solution from leaking from the syringe and from the ampoule during preparation of the solvent, while maintaining the sterility of the cannula, by protecting it from contaminating surfaces.

In order to prevent solution from leaking into bag 4 if the ampoule 1 is turned upside down there may be inserted a hygroscopic filter in the hose 5 which permits air to pass but which will be tightened by the surface tension of solution if the solution reaches the filter. Air can then pass again when the suction increases in the ampoule.

The described arrangement of apparatus enables harmful solutions to be prepared in a safe and reliable manner, while the simplicity of the arrangement renders it suitable for use as a protective means within the medical field.

What I claim is:

1. In an apparatus for preventing unintentional escape of solutions made from such harmful substances as cytostaticum, toxic, radioactive and allergy-producing substances, the combination comprising:

(a) a first container means for containing said solutions, said first container means having an interior, (b) first hermetically sealed means movable into and out of said first container means for withdrawing a solution therefrom, and (c) an expandable second container means fluidly cooperating with said first container means to equalize pressure in said first container means, said first container means being exterior to said second container means, said second container means being hermetically sealed and said second container means having an interior in constant fluid communication with the interior of said first container means, the interior of said first container means and the interior of said second container means defining a closed system having a finite volume of air so that as solution is withdrawn from said first container means by said first hermetically sealed means air is drawn from said second container means into said first container means to equalize pressure in said first container means.

2. The apparatus of claim 1 which includes a hose hermetically connecting the interior of said expandable second container means with the interior of said first container means to provide said fluid communication therebetween.

3. The apparatus of claim 1 wherein said expandable second container means comprises a bag made of flexible material.

4. The apparatus of claim 1:

(a) wherein said first hermetically sealed means comprises a cannula, (b) and a tubular sheath of elastic material housing said cannula for constantly protecting said cannula from contact with surrounding surfaces.

5. The apparatus of claim 4 wherein said cannula may be introduced into said first container means and wherein the apparatus includes a self-sealing thickened portion disposed on an end of said tubular sheath for sealingly abutting the top of said first container means when said cannula is introduced into said first container means.

* * * * *